United States Patent
Ozaki et al.

(10) Patent No.: US 7,638,506 B2
(45) Date of Patent: Dec. 29, 2009

(54) GRANULAR AGROCHEMICAL COMPOSITION

(75) Inventors: Eisuke Ozaki, Tokyo (JP); Kazunori Kurita, Tokyo (JP); Tetsuo Ohkawa, Tokyo (JP)

(73) Assignee: Kumiai Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 11/645,615

(22) Filed: Dec. 27, 2006

(65) Prior Publication Data

US 2007/0105720 A1  May 10, 2007

Related U.S. Application Data

(63) Continuation of application No. 10/508,162, filed as application No. PCT/JP03/03542 on Mar. 24, 2003, now abandoned.

(30) Foreign Application Priority Data

Mar. 29, 2002 (JP) .............................. 2002-97125

(51) Int. Cl.
*A61K 31/655* (2006.01)
*A61K 9/14* (2006.01)
*A61K 33/08* (2006.01)
*A01N 51/00* (2006.01)
*A01N 25/00* (2006.01)
*A01N 59/06* (2006.01)
*A01N 47/36* (2006.01)

(52) U.S. Cl. ................. 514/157; 424/405; 424/489; 424/688; 504/211

(58) Field of Classification Search .......... None
See application file for complete search history.

(56) References Cited

U.S. PATENT DOCUMENTS

| 4,657,581 | A | * | 4/1987 | Takematsu et al. ......... 504/336 |
| 4,844,734 | A | * | 7/1989 | Iwasaki et al. ............. 504/330 |
| 5,024,693 | A |   | 6/1991 | Gates et al. |
| 5,209,771 | A |   | 5/1993 | Meyer |
| 5,441,923 | A | * | 8/1995 | Tocker ...................... 504/125 |
| 5,693,593 | A |   | 12/1997 | Arnold |
| 5,707,926 | A |   | 1/1998 | Frisch et al. |
| 6,458,748 | B1 |  | 10/2002 | Yoshimura et al. |

FOREIGN PATENT DOCUMENTS

| CN | 1069392 A | 3/1993 |
| GB | 0512739 | 11/1992 |
| JP | 62-161702 | 7/1987 |
| JP | 63-035504 | 2/1988 |
| JP | 63-045201 | 2/1988 |
| JP | 02-288803 | 11/1990 |
| JP | 03-072407 | 3/1991 |
| JP | 4-198106 | 7/1992 |
| JP | 8-175904 | 7/1996 |
| WO | 93/00011 | 1/1993 |
| WO | 00/06553 | 2/2000 |

* cited by examiner

*Primary Examiner*—Ernst V Arnold
(74) *Attorney, Agent, or Firm*—Wenderoth, Lind & Ponack, L.L.P.

(57) ABSTRACT

Provided is a granular agrochemical composition by which the problems accompanying the prior art granular agrochemical compositions can be overcome, which can be prepared in a simple formulation and by which sustained releasability of the agrochemically active ingredient is obtained so that the load on the environments can be decreased and the chemical damages caused by the agrochemically active ingredient can be alleviated or prevented. The granular agrochemical composition contains an acidic agrochemically active ingredient, a cationic surfactant and a basic substance. Inter alia, a pH of 5 or higher is obtained in a 1% by mass aqueous suspension thereof. Preferably, the acidic agrochemically active ingredient should have a pKa of 2 to 7 and the cationic surfactant should be one which is gelled or exhibits swellability in water.

8 Claims, No Drawings

GRANULAR AGROCHEMICAL COMPOSITION

This is continuation of Ser. No. 10/508,162, filed Sep. 17, 2004, now abandoned, which is a 371 of PCT/JP2003/003542, filed Mar. 24, 2003.

TECHNICAL FIELD

The invention relates to a granular agrochemical composition capable of alleviating or preventing chemical damages and decreasing environmental load along with capability of exhibiting efficacy over a long duration.

BACKGROUND ART

Conventionally, to alleviate chemical damages of granular agrochemical compositions containing agrochemically active ingredients and to retain the effectiveness, various methods for formulation capable of controlling dissolution of the agrochemically active ingredients have been studied. There have been proposed many methods including, for example, methods imparting sustained releasability by the addition of a paraffin wax, activated carbon, foamed granules and clay type minerals in combination (Japanese Patent Application Laid-Open Nos. 63-35504, 63-45201 and 2-288803), methods of blending dymron to alleviate chemical damages of sulfonylurea-based compounds (Japanese Patent Application Laid-Open Nos. 62-161702 and 3-72407).

However, such prior art methods for imparting sustained releasability are not necessarily effective and there are problems that the preparation methods of the granular agrochemical compositions are complicated: and that a large portion of the agrochemically active ingredient remained unutilized effectively in the granular agrochemical composition due to insufficient release of the agrochemical composition. In the case of the methods of adding other agrochemically active ingredients such as dymron for alleviate chemical damages of a certain agrochemically active ingredient, there is a problem that agrochemically active ingredients are released more than needed to the environments, resulting in an increase in the load on the environments.

DISCLOSURE OF THE INVENTION

Under these circumstances, the invention has an object to overcome the problems of conventional granular agrochemical compositions and to provide a granular agrochemical composition which can be prepared in a simple formulation, capable of showing the efficacy of the agrochemically active ingredients over a long time, decreasing the environmental load, and alleviating or preventing chemical damages caused by the agrochemically active ingredients.

The inventors have conducted extensive investigations on a granular agrochemical composition, as a result, to find that the above-mentioned problems can be solved by obtaining a composition by compounding an acidic agrochemically active ingredient with a cationic surfactant and a basic substance and have accomplished the invention based on this finding.

That is, the invention provides the following compositions including:

(1) a granular agrochemical composition characterized by containing an acidic agrochemically active ingredient, a cationic surfactant and a basic substance;

(2) a granular agrochemical composition described in (1) above, wherein the acidic agrochemically active ingredient has a pKa in the range of 2 to 7;

(3) a granular agrochemical composition described in (1) or (2) above, wherein the cationic surfactant causes gelation or shows swelling in water;

(4) a granular agrochemical composition described in either one of (1), (2) or (3) above, wherein the acidic agrochemically active ingredient is a herbicide;

(5) a granular agrochemical composition described in (4) above, wherein the herbicide is a sulfonylurea-based compound;

(6) a granular agrochemical composition described in (4) above, wherein the herbicide is a difluoromethanesulfonylanilide derivative or a salt thereof expressed by the general formula (I):

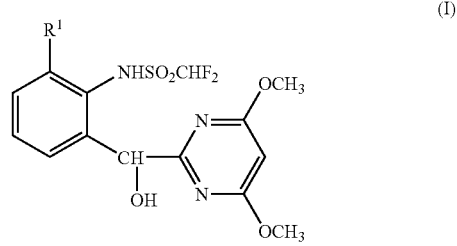

(wherein $R^1$ is a hydrogen atom, alkyl group or alkoxyalkyl group);

(7) a granular agrochemical composition described in either one of (1) to (6) above, wherein a 1% by mass aqueous suspension thereof has a pH 5 or higher;

(8) a granular agrochemical composition described in either one of (1) to (7) above, wherein a 1% by mass aqueous suspension thereof has a pH which is equal to or higher than the pKa value of the agrochemically active ingredient; and (9) a mixed granular agrochemical composition which is a blend of the granular agrochemical composition described in either one of the descriptions (1) to (8) above and agrochemical granules without containing either one or both of the cationic surfactant and the basic substance in a ratio of from 1:9 to 9:1 by mass.

BEST MODE FOR CARRYING OUT THE INVENTION

The type of an acidic agrochemically active ingredient to be used for the granular agrochemical composition of the invention is not particularly limited, however, it is generally a herbicide, a plant growth regulator, a fungicide, or an insecticide and specially, those having a pKa in the range of 2 to 7 are preferable and geometrical isomers and optical isomers are also included.

The herbicide is not particularly limited and those having a pKa in the range of 2 to 7 are preferable and especially, those comprising mainly sulfonylurea-based compounds, or difluoromethanesulfonylanilide derivatives expressed by the general formula (I):

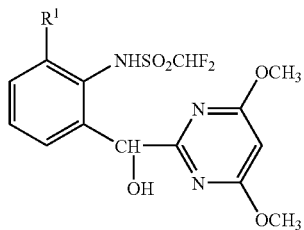

(I)

(wherein R[1] is a hydrogen atom, alkyl group or alkoxyalkyl group);

or salts thereof are further preferable.

Examples of the sulfonylurea-based compound include 1-(4,6-dimethoxypyrimidin-2-yl)-3-[1-methyl-4-(2-methyl-2H-tetrazol-5-yl)pyrazol-5-ylsulfonyl]urea (Azimsulfuron), 1-(2-chloroimidazo[1,2-a]pyridin-3-ylsulfonyl)-3-(4,6-dimethoxypyrimidin-2-yl)urea (imazosulfuron), ethyl 5-(4,6-dimethoxypyrimidin-2-ylcarbamoylsulfamoyl)-1-methylpyrazole-4-carboxylate (pyrazosulfuron-ethyl), methyl α-(4,6-dimethoxypyrimidin-2-ylcarbamoylsulfamoyl)-o-toluate(bensulfuron-methyl), 1-(4,6-dimethoxypyrimidin-2-yl)-3-(2-ethoxyphenoxysulfonyl)urea (ethoxysulfuron), 1-[2-(cyclopropylcarbonyl)aniline-sulfonyl]-3-(4,6-dimethoxypyrimidin-2-yl)urea (cyclosulfamuron), 1-(4,6-dimethoxy-1,3,5-triazin-2-yl)-3-[2-(2-methoxyethoxy)phenylsulfonyl]urea (cinosulfuron), methyl 3-(4-methoxy-6-methyl-1,3,5-triazin-2-ylcarbamoylsulfamoyl)-2-thenoate (thifensulfuron-methyl), 2-(4,6-dimethoxypyrimidin-2-ylcarbamoylsulfamoyl)-N,N-dimethylnicotinamide (nicosulfron), methyl 3-chloro-5-(4,6-dimethoxypyrimidin-2-ylcarbamoylsulfamoyl)-1-methylpyrazole-4-carboxylate (halosulfuron-methyl), 1-(4,6-dimethoxypyrimidin-2-yl)-3-(3-trifluoromethyl-2-pyridylsulfonyl)urea (flazasulfuron) and 1-(4,6-dimethoxypyrimidin-2-yl)-3-(3-ethylsulfonyl-2-pyridylsulfonyl)urea (rimsulfuron).

Examples of the difluoromethanesulfonylanilide derivatives and salts thereof include compounds described in Japanese Patent Application Laid-Open No. 2000-44546, such as 2-[(4,6-dimethoxypyrimidin-2-yl)hydroxymethyl]-N-difluoromethanesulfonylanilide, 2-[(4,6-dimethoxypyrimidin-2-yl)hydroxymethyl]-6-methoxymethyl-N-difuloromethanesulfonylanilide and 2-[(4,6-dimethoxypyrimidin-2-yl)hydroxymethyl]-6-ethyl-N-difuloromethanesulfonylanilide.

Examples of other herbicides include S-ethyl 2-methyl-4-chlrophenoxythioacetate (phenothiol), α-2-naphthoxypropionanilide (naproanilide), methyl 5-(2,4-dichlorophenoxy)-2-nitrobenzoate (bifenox), S-(4-chlorobenzyl)-N,N-diethylthiocarbamate (benthiocarb), S-benzyl 1,2-dimethylpropyl(ethyl)thiocarbamate (esprocarb), S-ethyl hexahydro-1H-azepine-1-carbothioate (molinate), S-1-methyl-1-phenylethyl piperidine-1-carbothioate (dimepiperate), O-3-tert-butylphenyl 6-methoxy-2-pyridyl(methyl)thiocarbamate (pyributicarb), 2-chloro-2',6'-diethyl-N-(2-butoxymethyl)acetanilide (butachlor), 2-chloro-2',6'-diethyl-N-(2-propoxyethyl)acetanilide (pretilachlor), (RS)-2-bromo-N-(α,α-dimethylbenzyl)-3,3-dimethylbutyramide (bromobutide), 2-benzothiazol-2-yloxy-N-methylacetanilide (mefenacet), 1-(α,α-dimethylbenzyl)-3-(p-tolyl)urea (dymron), 2-methylthio-4,6-bis(ethylamino)-s-triazine(simetryn), 2-methylthio-4,6-bis(isopropyl-amino)-s-triazine (prometryn), 2-methylthio-4-ethylamino-6-(1,2-dimethylpropylamino)-s-triazine(dimethametryn), 2,4-dichlorophenyl-3'-methoxy-4'-nitrophenyl ether (chlometoxyfen), 5-tert-butyl-3-(2,4-dichloro-5-isopropoxyphenyl)-1,3,4-oxadiazol-2(3H)-one (oxadiazon), 4-(2,4-dichlorobenzoyl)-1,3-dimethyl-5-pyrazolyl-p-toluene-sulfonate(pyrazolynate), 2-[4-(2,4-dichloro-benzoyl)-1,3-dimethylpyrazol-5-yloxy]acetophenone (pyrazoxyfen), (RS)-2-(2,4-dichloro-m-tolyloxy)propion-anilide (clomeprop), 2-[4-(2,4-dichloro-m-toluoyl)-1,3-dimethylpyrazol-5-yloxy]-4'-methylacetophenone (benzofenap), S,S'-dimethyl 2-difluoromethyl-4-isobutyl-6-trifluoromethylpyridine-3,5-dicarbothioate (dithiopyr), 2-chloro-N-(3-methoxy-2-thenyl)-2',6'-dimethylacetanilide (thenylchlor), butyl (R)-2-[4-(4-cyano-2-fluorophenoxy)-phenoxy]Propionate (cyhalofop-butyl), 3-[1-(3,5-dichlorophenyl)-1-methylethyl]-2,3-dihydro-6-methyl-5-phenyl-4H-1,3-oxazin-4-one (oxadichlomefon), 3-(4-chloro-5-cyclopentyloxy-2-fluorophenyl)-5-isopropylidene-1,3-oxazolidine-2,4-dione (pentoxazone), 1-(diethylcarbamoyl)-3-(2,4,6-trimethylphenylsulfonyl)-1,2,4-triazole (cafenstrole) and methyl 2-[(4,6-dimethoxypyrimidin-2-yl)oxy]-6-[(E)-1-(methoxyimino)ethyl]benzoate (pyriminobac-methyl).

The plant growth regulator is not particularly limited and examples thereof include 4'-chloro-2'-(α-hydroxybenzyl)isonicotinanilide(inabenfide), (2RS,3RS)-1-(4-chlorophenyl)-4,4-dimethyl-2-(1H-1,2,4-triazol-1-yl)-pentan-3-ol(paclobutrazol), (E)-(S)-1-(4-chlorophenyl)-4,4-dimethyl-2-(1H-1,2,4-triazol-1-yl)pent-1-en-3-ol (uniconazole), calcium 3-oxido-5-oxo-4-propionylcyclohexa-3-enecarboxylate(prohexadione-calcium) and choline salt of maleic hydrazide. Among these, those having a pKa in the range of 2 to 7 are preferably used.

The fungicide is not particularly limited and examples thereof include O,O-diisopropyl s-benzyl thio-phosphate (iprobenfos), 3'-isopropoxy-2-methylbenzanilide (mepronil), α,α,α-trifluoro-3'-isopropoxy-O-toluanilide (fultolanil), 3,4,5,6-tetrachloro-N-(2,3-dichlorophenyl)-phthalamic acid (tecloftalam), 1-(4-chlorobenzyl)-1-cyclopentyl-3-phenylurea(pencycuron), 6-(3,5-dichloro-4-methylphenyl)-3(2H)-pyridazinone(diclomezine), methyl N-(2-methoxyacetyl)-N-(2,6-xylyl)-DL-alaninate (metalaxyl), (E)-4-chloro-α,α,α-trifluoro-N-(1-imidazol-1-yl-2-propoxyethylidene)-o-toluidine(trifulmizole), kasugamycin, validamycin, 3-allyloxy-1,2-benzoisothiazole 1,1-dioxide (probenazole), diisopropyl 1,3-dithiolan-2-ylidenemalonate (isoprothiolane), 5-methyl-1,2,4-triazolo[3,4-b]benzothiazole (tricyclazole), 1,2,5,6-tetrahydropyroro[3,2,1-ij]quinolin-4-one (pyroquilon), 5-ethyl-5,8-dihydro-8-oxo[1,3]dioxolo[4,5-g]quinoline-7-carboxylic acid (oxolinic acid), (Z)-2'-methylacetophenone 4,6-dimethyl-pyrimidin-2-ylhydrazone-4,5,6,7-tetrachlorophtalide (ferimzone) and 3-(3,5-dichlorophenyl)-N-isopropyl-2,4-dioxoimidazolidine-1-carboxamide (iprodione). Among these, those having a pKa in the range of 2 to 7 are preferably used.

The insecticide is not particularly limited and examples thereof include O,O-dimethyl O-(3-methyl-4-nitrophenyl) thiophosphate (MEP), (2-isopropyl-4-methylpyrimidin-6-yl)-diethylthiophosphate (diazinon), 1-naphthyl N-methylcarbamate (carbaryl), O,O-diethyl O-(3-oxo-2-phenyl-2H-pyridazin-6-yl)phosphorothioate (pyridaphenthion), O,O-dimethyl O-3,5,6-trichloro-2-pyridyl phosphorothioate (chlorpyrifos-methyl), dimethyl dicarbethoxyethyl dithiophosphate (malathion), O,O-dimethyl S-(N-methylcarbamoylmethyl) dithiophosphate (dimethoate), O,O-dipropyl O-4-methylthiophenyl phosphate (propaphos), O,S-dimethyl N-acetylphosphoroamidothioate (acephate), ethyl p-nitrophenyl thionobenzenephosphonate (EPN), 2-sec-butylphenyl N-methylcarbamate (BPMC), 2,3-dihydro-2,2-dimethyl-7-benzo[b]furanyl N-dibutylaminothio-N-methylcarbamate (carbosulfan), ethyl N-[2,3-dihydro-2,2-dimethylbenzofuran-7-yloxycarbonyl(methyl)aminothio]-N-isopropyl-β-alaninate (benfuracarb), (RS)-α-cyano-3-phenoxybenzyl (RS)-2,2-dichloro-1-(4-ethoxyphenyl) Cyclopropanecarboxylate (cycloprothrin), 2-(4-ethoxy-phenyl)-2-methylpropyl 3-phenoxybenzyl ether (etofenprox), 1,3-bis(carbamoylthio)-2-(N,N-dimethylamino)propane hydrochloride (cartap), 5-dimethylamino-1,2,3-trithiane hydrogen oxalate (thiocyclam), S,S'-2-dimethylaminotri-methylene di(benzenthiosulfonate) (bensultap) and 2-tert-butylimino-3-isopropyl-5-phenyl-1,3,5,6-tetrahydro-2H-1,3,5-thiadiazin-4-one (buprofezin). Among these, those having a pKa in the range of 2 to 7 are preferably used.

In the case of using the above-described acidic agrochemically active ingredient having the prescribed pKa, the pKa of the ingredient can be measured by, for example, a method described in "Jikken Kagaku Koza 5, (Thermal measurement and Equilibrium)", Maruzene, p. 469-474, Jan. 20 (1958) and the like.

The cationic surfactant to be used in the invention is not particularly limited and can be exemplified preferably by those of amine salt type, pyridinium salt type and quaternary ammonium salt type.

Examples of the amine salt type cationic surfactants include laurylamine hydrochloride, stearylamine hydrochloride, oleylamine acetate, stearylamine acetate and stearylaminopropylamine acetate.

Examples of the pyridinium salt type cationic surfactants include laurylpyridinium chloride, myristylpyridinium chloride and cetylpyridinium chloride.

Examples of the quaternary ammonium salt type cationic surfactants include alkyldimethylbenzylammonium chloride, lauryltrimethylammonium chloride, cetyltri-methylammonium chloride, stearyltrimethylammonium chloride, dilauryldimethylammonium chloride, dioleyldimethylammonium chloride, dicocoyldimethylammonium chloride, distearyldimethylammonium chloride, lauryldi(hydroxyethyl)methylammonium chloride, oleylbis(polyoxyethylene)methylammonium chloride, stearylhydroxyethyldimethylammonium chloride, lauryldimethylbenzylammonium chloride, lauroylaminopropyl-dimethylethylammonium ethosulfate, and lauroylaminopropyl-dimethylhydroxyethylammonium perchlorate.

Those particularly preferable as the cationic surfactant are compounds which are gelled or exhibit swellability in water such as dialkyldimethylammonium chloride, the alkyl part of which is $C_8$ to $C_{22}$, particularly, dilauryldimethylammonium chloride, dioleyldimethylammonium chloride, dicocoyldimethylammonium chloride and distearyldimethylammonium chloride. These surfactants may be used either singly or in combination of two kinds or more.

The basic substance to be used in the invention is not particularly limited, however preferable are those having a pH 7.5 or higher or, more preferably 9 to 12, in the case that they are in the form of 1% by mass aqueous solution or 1% by mass aqueous suspension. Examples of the basic substances include hydroxides of alkali metals and alkaline earth metals, alkali metal salts, alkaline earth metal salts, and chemical substances and minerals containing them and more particular examples include sodium hydroxide, potassium hydroxide, sodium hydrogen carbonate, sodium carbonate, calcium hydroxide, calcium carbonate, calcium oxide, basic fumed silica and basic acid clay. These basic substances may be used either singly or in combination of two kinds or more.

The granular agrochemical composition of the invention may contain additive components used usually in agrochemical preparations, based on the necessity. As the additive-components, an extender or an auxiliary component may be used.

As the extender, a solid carrier such as a mineral carrier and a water-soluble salt may be used and particular examples thereof include clays, calcium carbonate, bentonite, talc, diatomaceous earth, acid clay, silica sand, granulated calcium carbonate, calcium stearate, fumed silica, potassium chloride, sodium sulfate anhydride, potassium sulfate, urea, ammonium sulfate and the like. These may be used either singly or in combination of two kinds or more.

As the auxiliary component, for example, a binder for preparing the granular composition may be included and particular examples include carboxymethyl cellulose sodium salt, dextrin, water-soluble starch, xanthan gum, guar gum, sucrose, poly(vinylpyrrolidone), poly(vinyl alcohol), poly (sodium acrylate), polyethylene glycol having an average molecular weight of 6,000 to 20,000 and polyethylene oxide having an average molecular weight of 100,000 to 5,000,000. Particular examples of the organic solvent to be used at the time of dissolving the acidic agrochemically active ingredient and the cationic surfactant and adsorption thereof on a carrier include alkylnaphthalenes, dimethylformamide, dimethyl sulfoxide, N-methyl-2-pyrrolidone, N-octylpyrrolidone and various polyhydric alcohols. Besides, according to need, stabilizers, inorganic hollow granules, plastic hollow granules and plant segments may be used. These may be used either singly or as a combination of two kinds or more.

The composition ratios of the respective components of the agrochemical granular composition of the invention are selected in the ranges, usually, as an acidic agrochemically active ingredient 0.01 to 50% by mass, a cationic surfactant 0.1 to 20% by mass and a basic substance 0.1 to 95% by mass and when the total amount of the foregoing three components does not reach 100%, the balance is an optional additive component. The composition ratios of the respective components are selected so that a pH of a 1% by mass aqueous suspension of the granular agrochemical composition is adjusted to 5 or higher, preferably, 7 or higher or, further preferably, 7.5 to 11.5 and especially that a pH of a 1% by mass aqueous suspension of the granular agrochemical composition indicates a value higher than the pKa of the agrochemically active ingredient or, particularly, in the range larger than the pKa value by 2 to 6.

In the case that the extender and auxiliary agents are contained, the contents in the total amount of the composition are generally selected in the ranges of 5 to 95% by mass for the extender and 0.1 to 30% by mass for the auxiliary agents.

The granular agrochemical composition of the invention is preferably to be a granular material having a particle diameter of 0.01 to 5 mm or, more preferably, 0.1 to 3 mm or having a diameter of 0.1 to 10 mm or, more preferably, 0.5 to 7 mm and a length of 0.3 to 30 mm or, more preferably, 1.5 to 20 mm.

While the granular agrochemical composition of the invention may be a type (a disintegration type) that granules are disintegrated and lose the master blend of granules by division or dispersion or may be a type (a non-disintegration type) that the granules are not disintegrated and keep granular master blend of granules, after treatment in a field, the non-disintegration type is preferable and especially the non-disintegration type which keep the master blend of granules, in which disintegration of the granules are not found or scarcely found even after 15 to 30 minutes from addition in water, is preferable.

Further, the non-disintegration type granular agrochemical composition of the invention can be added to disintegration type floating-in-water granules dispersing on water surface to obtain a saved agrochemical preparation having sustained releasability of dissolution of the agrochemically active ingredients.

The invention also includes a mixed granular agrochemical composition which is a blend of the above-mentioned granular agrochemical composition and agrochemical granules without containing either one or both of the cationic surfactant and the basic substance in a mass proportion of from 1:9 to 9:1.

A method for the preparation of the granular agrochemical composition of the invention is not particularly limited although, usually, the following methods may be employed:
- a method including steps of adding a suitable amount of water to a mixture of all of base materials, kneading the mixture, successively carrying out granulation by extruding the mixture through a screen having an opening of a specified size, and drying the granules;
- a method including steps of either dissolving an acidic agrochemically active ingredient and a cationic surfactant in an organic solvent and subjecting the mixture to be adsorbed on a basic carrier, or dissolving an acidic agrochemically active ingredient and a cationic surfactant in an organic solvent, subjecting the mixture adsorbed on a carrier and then subjecting same to be coated or adsorbed with a basic substance and, according to need, an agrochemically active ingredient having no sustained releasability; and
- a method including steps of mixing the granular agrochemical composition having sustained releasability obtained by the above-mentioned methods, an agrochemically active ingredient having no sustained releasability and auxiliary agents, kneading the mixture after addition of a suitable amount of water, carrying out granulation by extruding the mixture through a screen having mesh opening diameter larger than the particle diameter of the granules of the agrochemical composition having sustained releasability and drying the granules.

Hereinafter, the invention will be described in details with reference to Examples and Test Examples but the invention should not be limited to these Examples. Additionally, the term of parts in the respective Examples refers to parts by mass.

Each of the basic substances in Examples was used as a 1% by mass aqueous solution or 1% by mass aqueous suspension having a pH of 7.5 or higher.

Each of the cationic surfactants used in Examples 1, 3, 5 to 8, 10 and 12 to 25 caused gelation in water.

EXAMPLE 1

A 0.5 part portion of bensulfuron-methyl (pKa 5.03) and 5 parts of calcium carbonate were uniformly blended and crushed with a hammer mill. Together with the powder thus obtained, 2 parts of distearyldimethylammonium chloride, 3 parts of α starch and 89.5 parts of clay were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition having a diameter of 1.1 to 1.3 mm and a length of 3 to 7 mm and containing 0.5% by mass of bensulfuron-methyl (pH of a 1% by mass aqueous suspension 8.28). The granular agrochemical composition thus obtained was put into water and observed after 30 minutes for the disintegrability of the granules to obtain a result that it was of a non-disintegration type.

EXAMPLE 2

A 0.5 part portion of pyrazosulfuron-ethyl (pKa 3.91), 10 parts of clay and 0.2 part of sodium hydroxide were uniformly blended and crushed with a hammer mill. Together with the powder thus obtained, 2 parts of laurylamine hydrochloride, 5 parts of polyvinyl alcohol, 10.0 parts of sodium bentonite and 72.3 parts of clay were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition having a diameter of 1.1 to 1.3 mm and a length of 3 to 7 mm and containing 0.5% by mass of pyrazosulfuron-ethyl (pH of a 1% by mass aqueous suspension 10.51). The granular agrochemical composition thus obtained was put into water and observed after 30 minutes for the disintegrability of the granules to obtain a result that it was of a non-disintegration type.

EXAMPLE 3

A 0.5 part portion of the compound of the general formula (I) in which $R^1$ was a methoxymethyl group (hereinafter, referred to as Compound A, pKa 5.75), 2 parts of distearyldimethylammonium chloride, 3 parts of α starch and 94.5 parts of calcium carbonate were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition having a diameter of 1.1 to 1.3 mm and a length of 3 to 7 mm and containing 0.5% by mass of Compound A (pH of a 1% by mass aqueous suspension 9.08). The granular agrochemical composition thus obtained was put into water and observed after 30 minutes for the disintegrability of the granules to obtain a result that it was of a non-disintegration type.

EXAMPLE 4

A 0.3 part portion of bensulfuron-methyl (pKa 5.03), 0.06 part of azimsulfuron (pKa 3.60), 5 parts of stearyltrimethylammonium chloride, 5 parts of basic fumed silica, 2 parts of sodium polyacrylate and 87.64 parts of clay were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition having a diameter of 1.1 to 1.3 mm and a length of 3 to 7 mm and containing 0.3% by mass of bensulfuron-methyl and 0.06% by mass of azimsulfuron (pH of a 1% by mass aqueous suspension 10.28). The granular agrochemical composition thus obtained was put into water and observed after 30 minutes for the disintegrability of the granules to obtain a result that it was of a non-disintegration type.

EXAMPLE 5

A 0.5 part portion of Compound A (pKa 5.75), 3 parts of α starch and 96.5 parts of calcium carbonate were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition containing 0.5% by mass of Compound A. A 20 parts portion of the granular agrochemical composition and 80 parts of the granular agrochemical composition containing 0.5% by mass of Compound A in Example 3 were blended by a blender to obtain a mixed granular agrochemical composition having a diameter of 1.1 to 1.3 mm and a length of 3 to 7 mm and containing 0.5% by mass of Compound A (pH of a 1% by mass aqueous suspension 8.44). The granular agrochemical composition thus obtained was put into water and observed after 30 minutes for the disintegrability of the granules to obtain a result that it was of a non-disintegration type.

EXAMPLE 6

A 0.5 part portion of Compound A (pKa 5.75), 3 parts of α starch and 96.5 parts of calcium carbonate were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition containing 0.5% by mass of Compound A. A 50 parts portion of the granular agrochemical composition and 50 parts of the granular agrochemical composition containing 0.5% by mass of Compound A in Example 3 were blended by a blender to obtain a mixed granular agrochemical composition having a diameter of 1.1 to 1.3 mm and a length of 3 to 7 mm and containing 0.5% by mass of Compound A (pH of a 1% by mass aqueous suspension 8.90). The granular agrochemical composition thus obtained was put into water and observed after 30 minutes for the disintegrability of the granules to obtain a result that it was of a non-disintegration type.

EXAMPLE 7

A 0.5 part portion of Compound A (pKa 5.75), 3 parts of α starch and 96.5 parts of calcium carbonate were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition containing 0.5% by mass of Compound A. A 80 parts portion of the granular agrochemical composition and 20 parts of the granular agrochemical composition containing 0.5% by mass of Compound A in Example 3 were blended by a blender to obtain a mixed granular agrochemical composition having a diameter of 1.1 to 1.3 mm and a length of 3 to 7 mm and containing 0.5% by mass of Compound A (pH of a 1% by mass aqueous suspension 9.06). The granular agrochemical composition thus obtained was put into water and observed after 30 minutes for the disintegrability of the granules to obtain a result that it was of a non-disintegration type.

EXAMPLE 8

A 0.5 part portion of the compound of the general formula (I) in which $R^1$ was a ethyl group (hereinafter, referred to as Compound B, pKa 6.17), 5 parts of dilauryldimethylammonium chloride, 5 parts of basic fumed silica, 2 parts of sodium polyacrylate and 87.5 parts of clay were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition having a diameter of 1.1 to 1.3 mm and a length of 3 to 7 mm and containing 0.5% by mass of Compound B (pH of a 1% by mass aqueous suspension 10.41). The granular agrochemical composition thus obtained was put into water and observed after 30 minutes for the disintegrability of the granules to obtain a result that it was of a non-disintegration type.

EXAMPLE 9

A 0.5 part portion of bensulfuron-methyl (pKa 5.03), 10 parts of cetylpyridinium chloride and 8 parts of N-methyl-2-pyrrolidone were blended to obtain a bensulfuron-methyl solution. The bensulfuron-methyl solution prepared as above was added on 81.5 parts of basic acid clay, which had a particle size of 16 to 35 mesh (1000 to 425 µm) and gave a 1% by mass aqueous suspension having a pH of 7 to 10, to be adsorbed thereon for granulation to give granules of the agrochemical composition having a particle diameter of 0.4 to 1.1 mm and containing 0.5% by mass of bensulfuron-methyl (pH of a 1% by mass aqueous suspension 7.69). The granulated agrochemical composition thus obtained was put into water and observed after 30 minutes for the disintegrability of the granules to obtain a result that it was of a non-disintegration type.

EXAMPLE 10

A 3 parts portion of polyvinyl alcohol and 85.5 parts of calcium carbonate were uniformly blended in a high speed agitator and kneaded with addition of a suitable amount of water followed by extrusion by using a basket-type granulator through a screen of 1.2 mm mesh opening and the granulated material was dried by standing at 60° C. to obtain a base. Separately, 2 parts of fentrazamide and 2 parts of basic fumed silica were uniformly blended and crushed with a hammer mill to obtain fentrazamide-containing powder. A 0.5 part portion of Compound A (pKa 5.75), 2.0 parts of dilauryldimethylammonium chloride and 5 parts of tributyl phosphate were blended to obtain a Compound A solution. The base prepared as above was added to the Compound A solution to be adsorbed thereon for granulation and coated with the fentrazamide-containing powder to give granules of the agrochemical composition having a particle diameter of 1.1 to 1.3 mm and a length of 3 to 7 mm and containing 2% by mass of fentrazamide (pH of a 1% by mass aqueous suspension 9.45). The granular agrochemical composition thus obtained was put into water and observed after 30 minutes for the disintegrability of the granules to obtain a result that it was of a non-disintegration type.

EXAMPLE 11

A 2.5 parts portion of pentoxazone and 2 parts of calcium carbonate were uniformly blended and crushed with a hammer mill to obtain pentoxazone-containing powder. A 0.5 part portion of imazosulfuron (pKa 4.00), 5 parts of cetyltrimethylammonium chloride, 5 parts of dimethyl sulfoxide and 10 parts of dimethyl naphthalene were blended to obtain an imazosulfuron solution. Further, the imazosulfuron solution prepared as above was added to 75 parts of granulated bentonite, which had a particle size of 12 to 42 mesh (1400 to 355 µm) and gave a 1% by mass aqueous suspension having a pH of 9 to 10, to be adsorbed thereon for granulation and, then, coated with pentoxazone-containing powder to give granules of the agrochemical composition having a particle diameter of 0.3 to 1.5 mm and containing 0.5% by mass of imazosulfuron and 2.5% by mass of pentoxazone (pH of a 1% by mass aqueous suspension 7.96). The granular agrochemical composition thus obtained was put into water and observed after 30 minutes for the disintegrability of the granules to obtain a result that it was of a non-disintegration type.

EXAMPLE 12

A 2 parts portion of bensulfuron-methyl (pKa 5.03), 4 parts of distearyldimethylammonium chloride, 3 parts of polyvinyl alcohol, 2 parts of basic fumed silica and 15 parts of calcium carbonate were uniformly blended in a high speed agitator and kneaded with addition of a suitable amount of water followed by extrusion by using a basket-type granulator through a screen of 0.6 mm mesh opening and the granulated material was dried by standing at 60° C. to obtain a bensulfuron-methyl containing base having a diameter of 0.5 to 0.7 mm and a length of 1 to 6 mm. Together with the bensulfuron-methyl containing base, 2 parts of enzyme modified dextrin, 5 parts of sodium alkylnaphthalenesulfonate, 2 parts of sodium lauryl sulfate, 14 parts of hollow plastic bodies containing 85% by mass of moisture and 62.9 parts of sodium sulfate anhydride were uniformly blended in a high speed agitator and kneaded with addition of a suitable amount of water followed by extrusion by using a basket-type granulator through a screen of 5 mm mesh opening and the granulated material was dried by standing at 60° C. to obtain a granular agrochemical composition having a diameter of 3 to 7 mm and a length of 3 to 20 mm and containing 0.5% by mass of bensulfuron-methyl (pH of a 1% by mass aqueous suspension 8.85). The granular agrochemical composition thus obtained was put into water and observed after 30 minutes for the disintegrability of the granules to obtain results that the granular agrochemical composition having a diameter of 3 to 7 mm and a length of 3 to 20 mm disintegrated immediately after being put into water while the bensulfuron-methyl containing base having a diameter of 0.5 to 0.7 mm and a length of 1 to 6 mm and containing distearyldimethylammonium chloride, which is a cationic surface active agent, was of a non-disintegration type.

EXAMPLE 13

A 1 part portion of Compound B (pKa 6.17), 3 parts of dioleyldimethylammonium chloride and 5 parts of N-methyl-2-pyrrolidone were blended to obtain a Compound B solution. The Compound B solution prepared as above was added to 20 parts of basic acid clay, which had a particle size of 16 to 35 mesh (1000 to 425 μm) and gave a 1% aqueous suspension having a pH of 7 to 10, to be adsorbed thereon for granulation to give a Compound B containing base having a particle diameter of 0.4 to 1.1 mm. Together with the Compound B containing base, 1 part of Compound B, 0.5 part of sodium polyacrylate, 5 parts of sodium alkylnaphthalenesulfonate, 2 parts of dioctyl sulfosuccinate, 20 parts of hollow inorganic bodies and 42.5 parts of sodium benzoate were uniformly blended in a high speed agitator and kneaded with addition of a suitable amount of water followed by extrusion by using a basket-type granulator through a screen of 5 mm mesh opening and the granulated material was dried by standing at 60° C. to obtain a granular agrochemical composition having a diameter of 3 to 7 mm and a length of 3 to 20 mm and containing 2% by mass of Compound B (pH of a 1% by mass aqueous suspension 8.34). The granular agrochemical composition thus obtained was put into water and observed after 30 minutes for the disintegrability of the granules to obtain results that the granular agrochemical composition having a diameter of 3 to 7 mm and a length of 3 to 20 mm disintegrated immediately after being put into water while the Compound B containing base having a particle diameter of 0.4 to 1.1 mm and containing dioleyldimethylammonium chloride, which is a cationic surface active agent, was of a non-disintegration type.

EXAMPLE 14

A 0.5 part portion of Compound A (pKa 5.75), 1 part of distearyldimethylammonium chloride, 3 parts of α starch and 95.5 parts of calcium carbonate were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition having a diameter of 1.1 to 1.3 mm and a length of 3 to 7 mm and containing 0.5% by mass of Compound A (pH of a 1% by mass aqueous suspension 8.44). The granular agrochemical composition thus obtained was put into water and observed after 30 minutes for the disintegrability of the granules to obtain a result that it was of a non-disintegration type.

EXAMPLE 15

A 0.5 part portion of Compound A (pKa 5.75), 3 parts of distearyldimethylammonium chloride, 3 parts of α starch and 93.5 parts of calcium carbonate were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition having a diameter of 1.1 to 1.3 mm and a length of 3 to 7 mm and containing 0.5% by mass of Compound A (pH of a 1% by mass aqueous suspension 8.68). The granular agrochemical composition thus obtained was put into water and observed after 30 minutes for the disintegrability of the granules to obtain a result that it was of a non-disintegration type.

EXAMPLE 16

A 0.5 part portion of Compound A (pKa 5.75) and 5 parts of calcium carbonate were uniformly blended and crushed with a hammer mill. Together with the powder thus obtained, 2 parts of distearyldimethylammonium chloride, 3 parts of α starch and 89.5 parts of clay were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition having a diameter of 1.1 to 1.3 mm and a length of 3 to 7 mm and containing 0.5% by mass of Compound A (pH of a 1% by mass aqueous suspension 8.51). The granular agrochemical composition thus obtained was put into water and observed after 30 minutes for the disintegrability of the granules to obtain a result that it was of a non-disintegration type.

EXAMPLE 17

A 0.5 part portion of Compound B (pKa 6.17) and 5 parts of calcium carbonate were uniformly blended and crushed with a hammer mill. Together with the powder thus obtained, 2 parts of distearyldimethylammonium chloride, 3 parts of α starch and 89.5 parts of clay were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition having a diameter of 1.1 to 1.3 mm and a length of 3 to 7 mm and containing 0.5% by mass of Compound B (pH of a 1% by mass aqueous suspension 8.93). The granular agrochemical composition thus obtained was put into water and observed after 30 minutes for the disintegrability of the granules to obtain a result that it was of a non-disintegration type.

EXAMPLE 18

A 0.5 part portion of Compound B (pKa 6.17) and 1 part of calcium carbonate were uniformly blended and crushed with a hammer mill. Together with the powder thus obtained, 2 parts of dilauryldimethylammonium chloride, 3 parts of α starch and 93.5 parts of clay, which gave a 1% by weight aqueous suspension having a pH of 4.2, were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition having a diameter of 1.1 to 1.3 mm and a length of 3 to 7 mm and containing 0.5% by mass of Compound B (pH of a 1% by mass aqueous suspension 4.28). The granular agrochemical composition thus obtained was put into water and observed after 30 minutes for the disintegrability of the granules to obtain a result that it was of a non-disintegration type.

EXAMPLE 19

A 0.5 part portion of Compound B (pKa 6.17) and 5 parts of calcium carbonate were uniformly blended and crushed with a hammer mill. Together with the powder thus obtained, 2 parts of dilauryldimethylammonium chloride, 3 parts of α starch and 89.5 parts of clay, which gave a 1% by weight aqueous suspension having a pH of 4.2, were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition having a diameter of 1.1 to 1.3 mm and a length of 3 to 7 mm and containing 0.5% by mass of Compound B (pH of a 1% by mass aqueous suspension 5.81). The granular agrochemical composition thus obtained was put into water and observed after 30 minutes for the disintegrability of the granules to obtain a result that it was of a non-disintegration type.

EXAMPLE 20

A 0.5 part portion of Compound B (pKa 6.17) and 10 parts of calcium carbonate were uniformly blended and crushed with a hammer mill. Together with the powder thus obtained, 2 parts of dilauryldimethylammonium chloride, 3 parts of α starch and 84.5 parts of clay were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition having a diameter of 1.1 to 1.3 mm and a length of 3 to 7 mm and containing 0.5% by mass of Compound B (pH of a 1% by mass aqueous suspension 8.62). The granular agrochemical composition thus obtained was put into water and observed after 30 minutes for the disintegrability of the granules to obtain a result that it was of a non-disintegration type.

EXAMPLE 21

A 0.5 part portion of Compound A (pKa 5.75) and 1 part of calcium carbonate were uniformly blended and crushed with a hammer mill. Together with the powder thus obtained, 2 parts of dilauryldimethylammonium chloride, 3 parts of α starch and 93.5 parts of clay, which gave a 1% by weight aqueous suspension having a pH of 4.2, were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition having a diameter of 1.1 to 1.3 mm and a length of 3 to 7 mm and containing 0.5% by mass of Compound A (pH of a 1% by mass aqueous suspension 4.07). The granular agrochemical composition thus obtained was put into water and observed after 30 minutes for the disintegrability of the granules to obtain a result that it was of a non-disintegration type.

EXAMPLE 22

A 0.5 part portion of Compound A (pKa 5.75) and 5 parts of calcium carbonate were uniformly blended and crushed with a hammer mill. Together with the powder thus obtained, 2 parts of dilauryldimethylammonium chloride, 3 parts of α starch and 89.5 parts of clay were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition having a diameter of 1.1 to 1.3 mm and a length of 3 to 7 mm and containing 0.5% by mass of Compound A (pH of a 1% by mass aqueous suspension 8.51). The granular agrochemical composition thus obtained was put into water and observed after 30 minutes for the disintegrability of the granules to obtain a result that it was of a non-disintegration type.

EXAMPLE 23

A 2 parts portion of tricyclazole (pKa 1.6) and 5 parts of calcium carbonate were uniformly blended and crushed with a hammer mill. Together with the powder thus obtained, 2 parts of distearyldimethylammonium chloride, 3 parts of α starch and 88 parts of clay were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition having a diameter of 1.1 to 1.3 mm and a length of 3 to 7 mm and containing 2% by mass of tricyclazole (pH of a 1% by mass aqueous suspension 8.17). The granular agrochemical composition thus obtained was put into water and observed after 30 minutes for the disintegrability of the granules to obtain a result that it was of a non-disintegration type.

EXAMPLE 24

A 2 parts portion of EDDP (pKa 10.5), 5 parts of calcium carbonate and 1 part of fumed silica were uniformly blended and crushed with a hammer mill. Together with the powder thus obtained, 2 parts of distearyldimethylammonium chloride, 3 parts of α starch and 87 parts of clay were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition having a diameter of 1.1 to 1.3 mm and a length of 3 to 7 mm and containing 2% by mass of EDDP (pH of a 1% by mass aqueous suspension 7.53). The granular agrochemical composition thus obtained was put into water and observed after 30 minutes for the disintegrability of the granules to obtain a result that it was of a non-disintegration type.

EXAMPLE 25

A 2 parts portion of PHC (pKa 11.5) and 5 parts of calcium carbonate were uniformly blended and crushed with a hammer mill. Together with the powder thus obtained, 2 parts of distearyldimethylammonium chloride, 3 parts of α starch and 88 parts of clay were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition having a diameter of 1.1 to 1.3 mm and a length of 3 to 7 mm and containing 2% by mass of PHC (pH of a 1% by mass aqueous suspension 8.86). The granular agrochemical composition thus obtained was put into water and observed after 30 minutes for the disintegrability of the granules to obtain a result that it was of a non-disintegration type.

COMPARATIVE EXAMPLE 1

A 0.5 part portion of bensulfuron-methyl and 10.0 parts of calcium carbonate were uniformly blended and crushed with a hammer mill. Together with the powder thus obtained, 2 parts of sodium alkylbenzenesulfonate, 3 parts of α starch and 84.5 parts of clay were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition containing 0.5% by mass of bensulfuron-methyl and 2% by mass of sodium alkylbenzenesulfonate (pH of a 1% by mass aqueous suspension 8.35).

COMPARATIVE EXAMPLE 2

A 0.5 part portion of pyrazosulfuron-ethyl, 2 parts of paraffin (melting point 68 to 70° C.) and 1 part of basic fumed silica were blended under melting at 80° C. and, after being cooled to room temperature, crushed with a hammer mill. Together with the powder thus obtained, 3 parts of α starch, 25 parts of sodium bentonite and 68.5 parts of talc were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition containing 0.5% by mass of pyrazosulfuron-ethyl (pH of a 1% by mass aqueous suspension 9.35).

COMPARATIVE EXAMPLE 3

A 0.5 part portion of bensulfuron-methyl, 15 parts of sodium bentonite and 5 parts of activated carbon were uniformly blended and crushed with a hammer mill. Together with the powder thus obtained, 3 parts of α starch and 76.5 parts of talc were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition containing 0.5% by mass of bensulfuron-methyl (pH of a 1% by mass aqueous suspension 7.89).

COMPARATIVE EXAMPLE 4

A 0.5 part portion of bensulfuron-methyl and 8 parts of N-methyl-2-pyrrolidone were blended to obtain a bensulfuron-methyl solution. The bensulfuron-methyl solution prepared as above was added on 91.5 parts of a natural base of basic acid clays, which had a particle size of 16 to 35 mesh (1000 to 425 μm) and gave a 1% aqueous suspension having a pH of 7 to 10, to be adsorbed thereon for granulation to give granules of the agrochemical composition containing 0.5% by mass of bensulfuron-methyl (pH of a 1% by mass aqueous suspension 8.39).

COMPARATIVE EXAMPLE 5

A 0.5 part portion of bensulfuron-methyl, 4.5 parts of dymron, 25 parts of sodium bentonite, 3 parts of α starch and 67 parts of talc were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition containing 0.5% by mass of bensulfuron-methyl and 4.5% by mass of dymron (pH of a 1% by mass aqueous suspension 9.12).

COMPARATIVE EXAMPLE 6

A 0.5 part portion of Compound A, 2 parts of sodium alkylbenzenesulfonate, 3 parts of α starch and 94.5 parts of calcium carbonate were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition containing 0.5% by mass of Compound A (pH of a 1% by mass aqueous suspension 8.85).

COMPARATIVE EXAMPLE 7

A 2 parts portion of bensulfuron-methyl, 3 parts of polyvinyl alcohol, 2 parts of basic fumed silica and 15 parts of calcium carbonate were uniformly blended in a high speed agitator and kneaded with addition of a suitable amount of water followed by extrusion by using a basket-type granulator through a screen of 0.6 mm mesh opening and the granulated material was dried by standing at 60° C. to obtain a bensulfuron-methyl containing base. Together with the bensulfuron-methyl containing base thus obtained, 2 parts of enzyme modified dextrin, 5 parts of sodium alkylnaphthalenesulfonate, 2 parts of sodium lauryl sulfate, 14 parts of hollow plastic bodies containing 85 parts of moisture and 66.9 parts of sodium sulfate anhydride were uniformly blended in a high speed agitator and kneaded with addition of a suitable amount of water followed by extrusion by using a basket-type granulator through a screen of 5 mm mesh opening and the granulated material was dried by standing at 60° C. to obtain a granular agrochemical composition containing 0.5% by mass of bensulfuron-methyl (pH of a 1% by mass aqueous suspension 8.89).

COMPARATIVE EXAMPLE 8

A 2 parts portion of Compound B, 3 parts of polyvinyl alcohol, 2 parts of basic fumed silica and 15 parts of calcium carbonate were uniformly blended in a high speed agitator and kneaded with addition of a suitable amount of water followed by extrusion by using a basket-type granulator through a screen of 0.6 mm mesh opening and the granulated material was dried by standing at 60° C. to obtain a bensulfuron-methyl containing base. Together with the bensulfuron-methyl containing base thus obtained, 2 parts of enzyme modified dextrin, 5 parts of sodium alkylnaphthalene-sulfonate, 2 parts of sodium lauryl sulfate, 14 parts of hollow plastic bodies containing 85 parts of moisture and 66.9 parts of sodium sulfate anhydride were uniformly blended in a high speed agitator and kneaded with addition of a suitable amount of water followed by extrusion by using a basket-type granulator through a screen of 5 mm mesh opening and the granulated material was dried by standing at 60° C. to obtain a granular agrochemical composition containing 2% by mass of Compound B (pH of a 1% by mass aqueous suspension 9.80).

COMPARATIVE EXAMPLE 9

A 0.5 part portion of bensulfuron-methyl (pKa 5.03) and 5 parts of calcium carbonate were uniformly blended and crushed with a hammer mill. Together with the powder thus obtained, 3 parts of α starch and 91.5 parts of clay were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition containing 0.5% by mass of bensulfuron-methyl (pH of a 1% by mass aqueous suspension 9.01). The granular agrochemical composition thus obtained was put into water and observed after 30 minutes for the disintegrability of the granules to obtain a result that it was of a non-disintegration type.

COMPARATIVE EXAMPLE 10

A 0.5 part portion of Compound A (pKa 5.75) and 5 parts of calcium carbonate were uniformly blended and crushed with a hammer mill. Together with the powder thus obtained, 3 parts of α starch and 91.5 parts of clay were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition having a diameter of 1.1 to 1.3 mm and a length of 3 to 7 mm and containing 0.5% by mass of Compound A (pH of a 1% by mass aqueous suspension 8.68). The granular agrochemical composition thus obtained was put into water and observed after 30 minutes for the disintegrability of the granules to obtain a result that it was of a non-disintegration type.

COMPARATIVE EXAMPLE 11

A 0.5 part portion of Compound A (pKa 5.75), 2 parts of dilauryldimethylammonium chloride, 3 parts of α starch and 94.5 parts of clay, which gave a 1% by weight aqueous suspension having a pH of 4.2, were uniformly blended and crushed with a hammer mill. The powder thus obtained was uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition having a diameter of 1.1 to 1.3 mm and a length of 3 to 7 mm and containing 0.5% by mass of Compound A (pH of a 1% by mass aqueous suspension 4.54). The granular agrochemical composition thus obtained was put into water and observed after 30 minutes for the disintegrability of the granules to obtain a result that it was of a non-disintegration type.

COMPARATIVE EXAMPLE 12

A 0.5 part portion of Compound B (pKa 6.17) and 5 parts of calcium carbonate were uniformly blended and crushed with a hammer mill. Together with the powder thus obtained, 3 parts of α starch and 91.5 parts of clay were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition having a diameter of 1.1 to 1.3 mm and a length of 3 to 7 mm and containing 0.5% by mass of Compound B (pH of a 1% by mass aqueous suspension 8.72). The granular agrochemical composition thus obtained was put into water and observed after 30 minutes for the disintegrability of the granules to obtain a result that it was of a non-disintegration type.

COMPARATIVE EXAMPLE 13

A 0.5 part portion of Compound B (pKa 6.17), 2 parts of dilauryldimethylammonium chloride, 3 parts of α starch and 94.5 parts of clay, which gave a 1% by weight aqueous suspension having a pH of 4.2, were uniformly blended and crushed with a hammer mill. The powder thus obtained was uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition having a diameter of 1.1 to 1.3 mm and a length of 3 to 7 mm and containing 0.5% by mass of Compound B (pH of a 1% by mass aqueous suspension 4.77). The granular agrochemical composition thus obtained was put into water and observed after 30 minutes for the disintegrability of the granules to obtain a result that it was of a non-disintegration type.

COMPARATIVE EXAMPLE 14

A 2 parts portion of tricyclazole (pKa 1.6) and 5 parts of calcium carbonate were uniformly blended and crushed with a hammer mill. Together with the powder thus obtained, 3 parts of α starch and 90 parts of clay were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition having a diameter of 1.1 to 1.3 mm and a length of 3 to 7 mm and containing 2% by mass of tricyclazole (pH of a 1% by mass aqueous suspension 8.79). The granular agrochemical composition thus obtained was put into water and observed after 30 minutes for the disintegrability of the granules to obtain a result that it was of a non-disintegration type.

COMPARATIVE EXAMPLE 15

A 2 parts portion of EDDP (pKa 10.5), 5 parts of calcium carbonate and 1 part of fumed silica were uniformly blended and crushed with a hammer mill. Together with the powder thus obtained, 3 parts of α starch and 89 parts of clay were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition having a diameter of 1.1 to 1.3 mm and a length of 3 to 7 mm and containing 2% by mass of EDDP (pH of a 1% by mass aqueous suspension 8.32). The granular agrochemical composition thus obtained was put into water and observed after 30 minutes for the disintegrability of the granules to obtain a result that it was of a non-disintegration type.

COMPARATIVE EXAMPLE 16

A 2 parts portion of PHC (pKa 11.5) and 5 parts of calcium carbonate were uniformly blended and crushed with a hammer mill. Together with the powder thus obtained, 3 parts of α starch and 90 parts of clay were uniformly blended in a high speed agitator and kneaded with addition of a suitable amount of water followed by extrusion by using a basket-type granulator through a screen of 1.2 mm mesh opening and the granulated material was dried by standing at 60° C. to obtain a granular agrochemical composition having a diameter of 1.1 to 1.3 mm and a length of 3 to 7 mm and containing 2% by mass of PHC (pH of a 1% by mass aqueous suspension 9.27). The granular agrochemical composition thus obtained was put into water and observed after 30 minutes for the disintegrability of the granules to obtain a result that it was of a non-disintegration type.

TEST EXAMPLE 1

In-Water Dissolution Test

Into a glass vessel having an inner diameter of 15 cm, 900 ml of hard water of degree 3 were taken to make up a depth of 5 cm. Each of the granular agrochemical compositions of Examples 1, 2, 4 and 8-11 and Comparative Examples 1-7 was added thereto in such an amount as to correspond to 1 kg per 10 ares. After 1, 3, 7, 21 and 35 days from the treatment, water was taken to determine the concentration of the active ingredient in water by analyzing with the high-performance liquid chromatography (HPLC) thereby to obtain the proportion relative to the overall content in the granular material as the dissolved ratio in water. The results are shown in Table 1.

As is understood from Table 1, the granular agrochemical composition in each Example, with respect to the sulfonylurea-based compound or difluoromethanesulfonylanilide derivative or salt thereof as the herbicide, which was the active ingredient of the agrochemical, had the dissolution ratio in water moving low in all of the tests one day through 35 days after the treatment as compared with the comparative examples excepting Comparative Examples 2 and 3.

In Comparative Examples 2 and 3, the in-water concentration moved low throughout indicating that dissolution of the agrochemically active ingredient was limited to the very beginning stage not to be continued. Accordingly they were apparently inferior because a large portion of the agrochemically active ingredient in the granular agrochemical composition remained unutilized.

TABLE 1

|  | Agrochemically active ingredient | Dissolved ratio in water (%) | | | | |
|---|---|---|---|---|---|---|
|  |  | 1 day | 3 days | 7 days | 21 days | 35 days |
| Example 1 | bensulfuron-methyl | 42 | 56 | 64 | 76 | 82 |
| Example 2 | pyrazosulfuron-ethyl | 58 | 72 | 80 | 83 | 86 |
| Example 4 | bensulfuron-methyl | 49 | 61 | 69 | 79 | 86 |
|  | azimsulfuron | 62 | 68 | 76 | 83 | 89 |
| Example 8 | Compound B | 25 | 32 | 40 | 45 | 50 |
| Example 9 | bensulfuron-methyl | 57 | 67 | 78 | 84 | 92 |
| Example 10 | Compound A | 19 | 23 | 31 | 35 | 41 |
|  | fentrazamide | 32 | 78 | 97 | 100 | 100 |
| Example 11 | imazosulfuron | 56 | 72 | 77 | 86 | 89 |
|  | Pentoxazone | 4 | 9 | 12 | 12 | 18 |
| Comparative Example 1 | bensulfuron-methyl | 98 | 100 | 100 | 100 | 100 |
| Comparative Example 2 | pyrazosulfuron-ethyl | 12 | 9 | 11 | 15 | 9 |
| Comparative Example 3 | bensulfuron-methyl | 4 | 0 | 3 | 0 | 0 |
| Comparative Example 4 | bensulfuron-methyl | 100 | 100 | 100 | 100 | 100 |
| Comparative Example 5 | bensulfuron-methyl | 97 | 100 | 100 | 100 | 100 |
|  | dymron | 27 | 51 | 68 | 82 | 94 |
| Comparative Example 6 | Compound A | 100 | 100 | 100 | 100 | 100 |
| Comparative Example 8 | Compound B | 99 | 100 | 100 | 100 | 100 |

TEST EXAMPLE 2

In-Water Dissolution: INFLUENCE of AMOUNT of CATIONIC SURFACTANT ADDED

Into a glass vessel having an inner diameter of 15 cm, 900 ml of hard water of degree 3 were taken to make up a depth of 5 cm. Each of the granular agrochemical compositions of Examples 3, 14 and 15 and Comparative Example 6 was added thereto in such an amount as to correspond to 1 kg per 10 ares. After 1, 3, 7, 21 and 35 days from the treatment, water was taken to determine the concentration of the active ingredient in water by the HPLC analysis as the dissolved ratio in water. The results are shown in Table 2.

It is understood from Table 2 that, as the content of the cationic surfactant in the granular agrochemical composition was increased, the dissolved ratio in water of the compound A was reduced moving low as compared with Comparative Example 6 where no cationic surfactant was added.

TABLE 2

|  | Content of cationic surfactant | Dissolved ratio in water (%) | | | | |
|---|---|---|---|---|---|---|
|  |  | 1 day | 3 days | 7 days | 21 days | 35 days |
| Example 14 | 1% | 33 | 48 | 56 | 67 | 71 |
| Example 3 | 2% | 24 | 31 | 42 | 46 | 50 |
| Example 15 | 3% | 12 | 18 | 22 | 29 | 33 |
| Comparative Example 6 | — | 99 | 97 | 100 | 100 | 100 |

TEST EXAMPLE 3

In-Water Dissolution: Control of Sustained Releasability

Into a glass vessel having an inner diameter of 15 cm, 900 ml of hard water of degree 3 were taken to make up a depth of 5 cm. Each of the granular agrochemical compositions of Examples 3, 5, 6 and 7 and Comparative Example 6 was added thereto in such an amount as to correspond to 1 kg per 10 ares. After 1, 3, 7, 21 and 35 days from the treatment, water was taken to determine the concentration of the active ingredient in water by the HPLC analysis as the dissolved ratio in water. The results are shown in Table 3.

It is understood from Table 3 that, as compared with the granular agrochemical composition of the Comparative Example without sustained releasability, the sustained releasability of the compound A could be controlled in the granular agrochemical compositions in the Examples.

TABLE 3

| | Dissolved ratio in water (%) | | | | |
|---|---|---|---|---|---|
| | 1 day | 3 days | 7 days | 21 days | 35 days |
| Example 3 | 20 | 28 | 38 | 42 | 47 |
| Example 5 | 33 | 41 | 49 | 55 | 60 |
| Example 6 | 58 | 62 | 67 | 71 | 72 |
| Example 7 | 82 | 86 | 90 | 91 | 95 |
| Comparative Example 6 | 100 | 100 | 99 | 100 | 100 |

TEST EXAMPLE 4

In-Water Dissolution

Into a 75 cm by 35 cm wide container, 9 liters of hard water of degree 3 were introduced to make up a depth of 5 cm. Each of the granular agrochemical compositions of Examples 12 and 13 and Comparative Examples 7 and 8 was applied for treatment in such an amount as to correspond to 0.25 kg per 10 ares. After 1, 3, 7, 21 and 35 days from the treatment, the water was taken to determine the concentration of the active ingredient in water by the HPLC analysis as the dissolved ratio in water. The results are shown in Table 4.

As is understood from Table 4, the in-water concentration in Examples moved low as compared with the Comparative Example indicating that the agrochemical active ingredient was imparted with sustained releasability.

TABLE 4

| | Agrochemically active ingredient | Dissolved ratio in water (%) | | | | |
|---|---|---|---|---|---|---|
| | | 1 day | 3 days | 7 days | 21 days | 35 days |
| Example 12 | bensulfuron-methyl | 48 | 58 | 65 | 71 | 74 |
| Example 13 | Compound B | 58 | 62 | 70 | 78 | 85 |
| Comparative Example 7 | bensulfuron-methyl | 100 | 100 | 100 | 100 | 100 |
| Comparative Example 8 | Compound B | 100 | 100 | 100 | 100 | 100 |

TEST EXAMPLE 5

Biological Effectiveness Test: Paddy Rice

A 100 $cm^2$ wide plastic pot was filled with a paddy field soil and, after watering and shuffling, seeds of each of early watergrass (*Echinochloa oryzoides*), heartshape false pickerelweed (*Monochoria vaginalis*) and HOTARU-I (*Scirpus juncoides*) were sowed in a depth of 0.5 cm. Further, two paddy rice plants at the two-leaves stage were transplanted in a transplanting depth of 2 cm followed by pooling of water in a depth of 5 cm. On the next day of transplantation, each of the granular agrochemical compositions obtained in Examples 3, 5, 6 and 7 and Comparative Example 6 was evenly applied for treatment in an amount relative to the amount of the effective ingredient corresponding to 5 g/10 ares by weighing. The plants on these plastic pots were grown in a greenhouse and, after 28 days, evaluation was made by the following criteria for the herbicidal effects and the extent of chemical damages. The results are shown in Table 5.

It is noted from Table 5 that the granular agrochemical compositions of the Examples exhibited excellent herbicidal effects almost without chemical damages to the paddy rice while considerable chemical damages were found in Comparative Example 6 against paddy rice.

Evaluation criteria for herbicidal effects (growth suppression and chemical damages 5: 90% or higher 4 or higher but lower than 5: 70% or higher but lower than 90%

3 or higher but lower than 4: 50% or higher but lower than 70%

2 or higher but lower than 3: 30% or higher but lower than 50%

1 or higher but lower than 2: 10% or higher but lower than 30%

0 or higher but lower than 1: 0% or higher but lower than 10%

TABLE 5

| | Herbicidal effects | | | Chemical damages paddy rice |
|---|---|---|---|---|
| | early watergrass | heartshape false pickerelweed | HOTARU-I | |
| Example 3 | 4.5 | 5.0 | 5.0 | 0 |
| Example 5 | 5.0 | 5.0 | 5.0 | 0 |
| Example 6 | 5.0 | 5.0 | 5.0 | 0.5 |
| Example 7 | 5.0 | 5.0 | 5.0 | 0.5 |
| Comparative Example 6 | 5.0 | 5.0 | 5.0 | 1.5 |

TEST EXAMPLE 6

Biological Effectiveness Test: Effect RETENTION TEST

A 200 $cm^2$ wide plastic pot filled with a paddy field soil was watered and the soil was shuffled followed by introduction of water to give a water depth of 5 cm and one of the granular agrochemical compositions obtained in Examples 5, 6 and 7 and comparative Example 6 was applied thereto by weighing in such an amount as to correspond to 2.5 g/10 ares relative to the amount of the effective ingredient. From just after this treatment, water leak was caused from the bottom of the plastic pot for 3 days at a rate of 2 cm per day and the water leak was followed by introduction of water from above the plastic pot to make up a water depth of 5 cm. On the 0th, 20th and 40th days from the treatment, respective seeds of early watergrass, heartshape false pickerelweed and HOTARU-I were sowed and growth of the weeds was observed on the 30th day from sowing. The evaluation criteria of the herbicidal effects were in accordance with those in Test Example 5. The results are shown in Table 6. It is understood from Table 6 that the granular agrochemical compositions in the Examples exhibited superior effect retention as compared with the Comparative Example.

TABLE 6

| | Herbicidal effects | | | | | | | | |
|---|---|---|---|---|---|---|---|---|---|
| | early watergrass | | | heartshape false pickerelweed | | | HOTARU-I | | |
| | 0 day | 20 days | 40 days | 0 day | 20 days | 40 days | 0 day | 20 days | 40 days |
| Example 5 | 4.3 | 4.5 | 4.0 | 4.7 | 4.9 | 4.5 | 4.7 | 4.9 | 4.8 |
| Example 6 | 4.5 | 4.5 | 3.5 | 4.9 | 4.8 | 4.5 | 4.8 | 4.9 | 4.5 |
| Example 7 | 4.8 | 4.5 | 3.7 | 4.9 | 4.3 | 3.5 | 4.9 | 4.8 | 4.5 |
| Comparative Example 6 | 4.3 | 3.5 | 3.0 | 4.8 | 4.3 | 3.0 | 4.8 | 4.8 | 3.7 |

TEST EXAMPLE 7

In-Water Dissolution

Into a glass vessel having an inner diameter of 15 cm, 900 ml of hard water of degree 3 were taken to make up a depth of 5 cm. Each of the granular agrochemical compositions of Examples 1, 16 and 17 and Comparative Examples 9, 10 and 12 was added thereto in such an amount as to correspond to 1 kg per 10 ares and each of the granular agrochemical compositions of Examples 23, 24 and 25 and Comparative Examples 14, 15 and 16 was added thereto in such an amount as to correspond to 3 kg per 10 ares. After 1, 3, 7, 21 and 35 days from the treatment, water was taken to determine the concentration of the active ingredient in water by the HPLC analysis as the dissolved ratio in water. The results are shown in Table 7.

Table 7 indicates that, when the pKa of the acidic agrochemically active ingredient was 2 to 7, the dissolved ratio in water of the compound A and compound B as a difluoromethane sulfonylanilide derivative in particular was strongly suppressed. An effect of suppressing dissolved ratio in water was also noted in Example 25 for an insecticidal agent and in Examples 23 and 24 for a bactericidal agent.

TABLE 7

| | Active ingredient | Dissolved ratio in water (%) | | | | |
|---|---|---|---|---|---|---|
| | | 1 day | 3 days | 7 days | 21 days | 35 days |
| Example23 | tricyclazole | 72 | 77 | 89 | 100 | 97 |
| Example1 | bensulfuron-methyl | 55 | 60 | 69 | 82 | 87 |
| Example16 | Compound A | 15 | 30 | 32 | 48 | 53 |

TABLE 7-continued

| | Active ingredient | Dissolved ratio in water (%) | | | | |
|---|---|---|---|---|---|---|
| | | 1 day | 3 days | 7 days | 21 days | 35 days |
| Example17 | Compound B | 11 | 28 | 25 | 35 | 44 |
| Example24 | EDDP | 6 | 11 | 21 | 25 | 23 |
| Example25 | PHC | 64 | 70 | 69 | 75 | 74 |
| Comparative Example14 | tricyclazole | 100 | 100 | 100 | 94 | 98 |
| Comparative Example9 | bensulfuron-methyl | 92 | 99 | 100 | 100 | 100 |
| Comparative Example10 | Compound A | 97 | 100 | 100 | 100 | 100 |
| Comparative Example12 | Compound B | 100 | 99 | 100 | 98 | 100 |
| Comparative Example15 | EDDP | 18 | 31 | 48 | 41 | 37 |
| Comparative Example16 | PHC | 81 | 100 | 95 | 91 | 89 |

TEST EXAMPLE 8

In-Water Dissolution

Into a glass vessel having an inner diameter of 15 cm, 900 ml of hard water of degree 3 were taken to make up a depth of 5 cm. Each of the granular agrochemical compositions of Examples 18, 19, 20, 21 and 22 and Comparative Examples 11 and 13 was added thereto in such an amount as to correspond to 1 kg per 10 ares. After 1, 3, 7, 21 and 35 days from the treatment, water was taken to determine the concentration of the active ingredient in water by the HPLC analysis as the dissolved ratio in water. The results are shown in Table 8.

Table 8 indicates that the dissolved ratio in water was suppressed by increasing the content of the basic substance while the dissolved ratio in water was suppressed when the pH of the granular agrochemical composition as a 1% by weight aqueous suspension was higher than the pKa of the acidic agrochemically active ingredient.

TABLE 8

| | Activate ingredient | Dissolved ratio in water (%) | | | | |
|---|---|---|---|---|---|---|
| | | 1 day | 3 days | 7 days | 21 days | 35 days |
| Example 18 | Compound B | 54 | 68 | 68 | 71 | 75 |
| Example 19 | Compound B | 42 | 59 | 55 | 61 | 65 |
| Example 20 | Compound B | 12 | 10 | 24 | 40 | 45 |
| Example 21 | Compound A | 39 | 54 | 47 | 52 | 75 |
| Example 22 | Compound A | 9 | 18 | 21 | 40 | 42 |
| Comparative Example 13 | Compound B | 82 | 87 | 95 | 100 | 96 |
| Comparative Example 11 | Compound A | 79 | 84 | 96 | 96 | 100 |

INDUSTRIAL APPLICABILITY

The granular agrochemical composition of the invention can be prepared in a simple formulation and can moderately impart sustained releasability to the dissolution of the agrochemically active ingredient, thereby, to exhibit the efficacy of the agrochemically ingredient over a long time and a remarkable effect can be obtained that, by decreasing the rate of release of the agrochemically ingredient into the environments, the load on the environments can be decreased and the chemical damages, such as the chemical damages against target crops, caused by the agrochemically active ingredient can be alleviated or prevented.

The invention claimed is:

1. A granular agrochemical composition comprising:
   (1) an acidic agrochemically active ingredient, which comprises one or more difluoromethanesulfonylanilide compounds, or salts thereof, described by the formula:

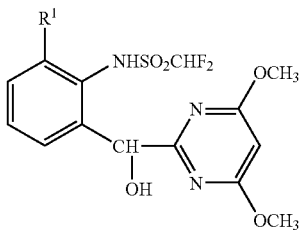

wherein $R^1$ is a hydrogen atom, alkyl group or alkoxyalkyl group;
   (2) a cationic surface-active agent which comprises one or more dialkyldimethylammonium chlorides, the alkyl part thereof being $C_8$ to $C_{22}$; and
   (3) a basic substance which comprised one or more of alkali of alkaline earth metal salts or hydroxides, calcium oxide, basic fumed silica or basic acid clay;
wherein said (1) and (2) are in a mass proportion of from 1:2 to 1:10; and further wherein the sustained releasability of dissolution of said (1) is controlled.

2. The granular agrochemical composition of claim 1, wherein $R^1$ is a methoxymethyl group.

3. The granular agrochemical composition of claim 1, wherein $R^1$ is an ethyl group.

4. the granular agrochemical composition of claim 1, wherein the basic substance comprises one or more of sodium hydroxide, potassium hydroxide, sodium hydrogen carbonate, sodium carbonate, calcium hydroxide, calcium carbonate, calcium oxide, basic fumed silica or basic acid clay.

5. the granular agrochemical composition of claim 1, wherein the basic substance comprises one or more of sodium carbonate, basic fumed silica or basic acid clay.

6. A mixed granular agrochemical composition which is a blend of a) the granular agrochemical composition of claim 1 and b) agrochemical granules of a) which do not contain either one or both of the cationic surface active agent and the basic substance.

7. The mixed granular agrochemical composition of claim 6, wherein said a) and b) are in a mass proportion from 1:9 to 9:1.

8. A method for the preparation of a granular agrochemical composition comprising:
   (1) an acidic agrochemically active ingredient, which comprises one or more difluoromethanesulfonylanilide compounds, or salts thereof, described by the formula:

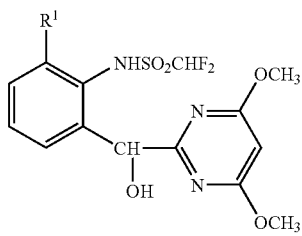

wherein $R^1$ is a hydrogen atom, alkyl group or alkoxyalkyl group;
   (2) a cationic surface-active agent which comprises one or more of dialkyldimethylammonium chlorides, the alkyl part thereof being $C_8$ to $C_{22}$; and
   (3) a basic substance which comprises one or more of alkali or alkaline earth metal salts or hydroxides, calcium oxide, basic fumed silica or basic acid clay;
wherein said (1) and (2) are in a mass proportion of from 1:2 to 1:10; and further wherein the sustained releasability of dissolution of said (1) is controlled;
   said method comprising the steps of adding a suitable amount of water to a mixture of said (1), (2) and (3), kneading the mixture, extruding the mixture through a screen having an opening of a specified size to create granules, and drying the granules.

* * * * *

UNITED STATES PATENT AND TRADEMARK OFFICE
CERTIFICATE OF CORRECTION

PATENT NO. : 7,638,506 B2  Page 1 of 2
APPLICATION NO. : 11/645615
DATED : December 29, 2009
INVENTOR(S) : Eisuke Ozaki et al.

It is certified that error appears in the above-identified patent and that said Letters Patent is hereby corrected as shown below:

In column 25, claim 1, lines 9-20:

The formula

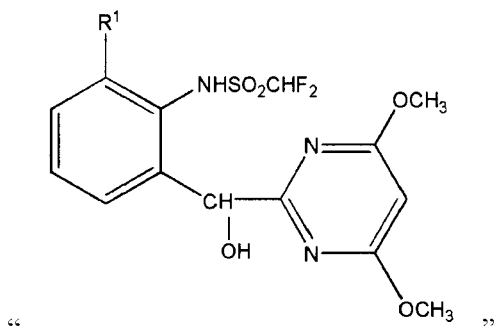

" "

should be

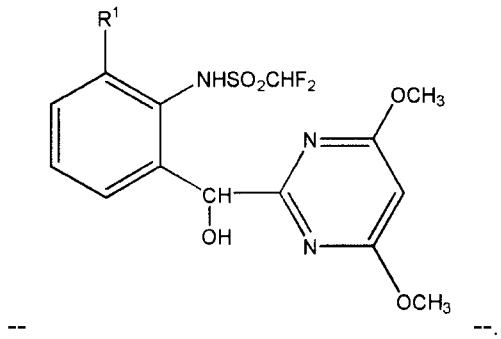

-- --.

In column 25, claim 1, line 26, "comprised" should be --comprises--.

In column 25, claim 1, line 27, "of" should be --or--.

In column 25, claim 4, line 36, "the" should be --The--.

In column 25, claim 5, line 41, "the" should be --The--.

CERTIFICATE OF CORRECTION (continued)
U.S. Pat. No. 7,638,506 B2

In column 26, claim 8, lines 14-25:

The formula

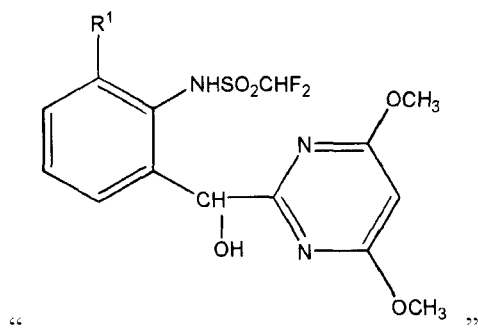

" "

should be

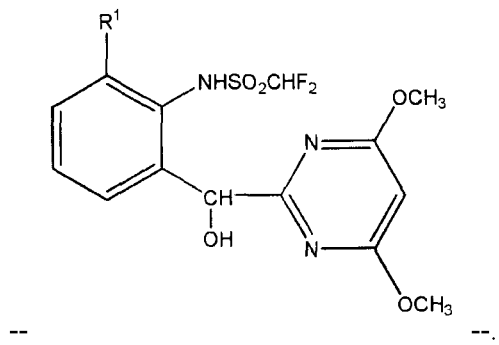

-- --.

Signed and Sealed this

Thirteenth Day of April, 2010

David J. Kappos
*Director of the United States Patent and Trademark Office*